United States Patent [19]

Storni

[11] Patent Number: 5,004,755
[45] Date of Patent: Apr. 2, 1991

[54] PHARMACEUTICAL USE OF LAEVOROTATORY BASIC DERIVATIVE OF 9,10-ETHANOANTHRACENE

[75] Inventor: Angelo Storni, Rheinfelden, Switzerland

[73] Assignee: Ciba-Geigy Corporation, Ardsley, N.Y.

[21] Appl. No.: 100,145

[22] Filed: Aug. 28, 1987

Related U.S. Application Data

[62] Division of Ser. No. 274,907, Jun. 18, 1981, abandoned.

[30] Foreign Application Priority Data

Feb. 2, 1979 [CH] Switzerland .................... 1046/79
Jan. 8, 1980 [CH] Switzerland ...................... 93/80

[51] Int. Cl.$^5$ .................................... A61K 31/135
[52] U.S. Cl. .................................. 514/653; 514/554;
514/556; 564/355; 564/384; 564/352
[58] Field of Search ............... 514/554, 556, 653;
564/384, 352, 355

[56] References Cited

U.S. PATENT DOCUMENTS 4,017,542  4/1977  Wilhelm et al. .................... 564/355

OTHER PUBLICATIONS

Burger, "Medicinal Chemistry", 3rd Ed., Part I, pp. 81–85 and 100–103 (1970).
E. Uschin et al., Frontiers in Neuropsychiat Research Ed. MacMillan, pp. 121–134 (1983).

Primary Examiner—Richard L. Raymond
Attorney, Agent, or Firm—Irving M. Fishman; JoAnn Villamizer

[57] ABSTRACT

The present invention relates to a new laevorotatory basic derivative of 9,10-ethanoanthracene, namely R-(−)-α-[(methylamino)methyl]-9,10-ethanoanthracene-9(10H)-ethanol of the formula I

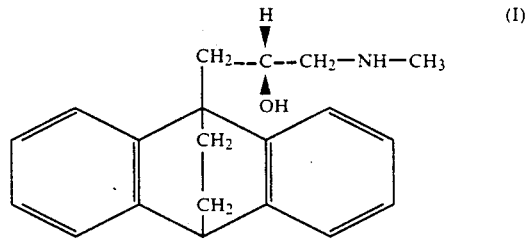

and the acid addition salts thereof, to pharmaceutical compositions containing these new substances and to a method for treating dysphoric conditions, psychovegetative or psychosomatic disorders.

9 Claims, No Drawings

PHARMACEUTICAL USE OF LAEVOROTATORY BASIC DERIVATIVE OF 9,10-ETHANOANTHRACENE

This is a divisional of application Ser. No. 274,907, filed on June 18, 1981, now abandoned.

The present invention relates to a new laevorotatory basic derivative of 9,10-ethanoanthracene and the acid addition salts thereof, to pharmaceutical compositions containing these new substances and to their use.

The compound of the invention is R-(−)-α-[(methylamino) methyl]-9,10-ethanoanthracene-9(10H)-ethanol of the formula

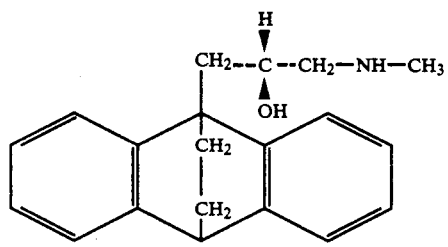

and is the (−)-antipode of the racemic α-[methylamino)methyl]-9,10-ethanoanthracene-9-(10H)-ethanol described in U.S. Pat. No. 4,017,542 and corresponding patent specifications of other countries having the Swiss priority of 23.2.1971. Acid addition salts of the compound of the formula I are in particular pharmaceutically acceptable salts, such as the hydrobromide, phosphate, methanesulfonate, ethanesulfonate, 2-hydroethanesulfonate, acetate, lactate, malonate, succinate, fumarate, maleate, malate, tartrate, citrate, benzoate, salicylate, phenylacetate, mandelate or embonate, and especially the hydrochloride, as well as in general readily crystallising salts with optically active acids, besides those already mentioned, e.g. also the (1:1) salt with bis-0,0'-(p-toluoyl)-L-tartaric acid. Because of the close relationship between the free base and its acid addition salts, reference to the base and to its acid addition salts will be understood by analogy as applying also to the acid addition salts and the free base respectively.

R-(−)-α-[(Methylamino)methyl]-9,10-ethanoanthracene-9(10H)-ethanol and its acid addition salts possess valuable pharmacological properties which differ in surprising manner from those of the known racemate and its acid addition salts. In contrast to the known racemate, they show in animal tests virtually no antagonism to reserpine and tetrabenazine and they also do not inhibit the uptake of noradrenaline in the heart and brain of rats and the noradrenaline depletion in the brain of rats caused by H77/77 (3-hydroxy-4-α-dimethylphenethylamine). As against this, the compound of the formula I and its acid addition salts have a sedative, antiaggressive and antihistiminic action of similar potency to that of the known racemate. When potentiating the anesthesia induced in mice by G 29505 [2-(4-allyl-2-methoxyphenoxy)-N,N-diethylacetamide, W. Theobald and R. Domenjoz, Arzneimittelforsch. 9, 285–286 (1959)] in order to determine the sedative action, the equivalent doses of the hydrochloride of the compound of formula I are about half as great as those of the hydrochloride of the racemate and thus the compound of the formula I is about twice as potent as the racemate, whereas in the aggressive reaction of male mice provoked by electric shock to the feet [Tedeschi et al., J.Pharmacol. Exptl. Therap. 125, 28–34, (1959)], the intraperitoneally administered equivalent doses of the hydrochloride of the compound of the formula I and of the racemate are of about the same magnitude, and when antagonising the histamine toxicity in guinea pigs, likewise by intraperitoneal adminstration, the hydrochloride of the racemate with an $ED_{50}$ of about 0.1 mg/kg is somewhat more potent than the hydrochloride of the compound of formula I with an $ED_{50}$ of about 0.25 mg/kg. The negatively inotropic action of the hydrochloride of the compound of the formula I on the isolated, electrically stimulated left atrium of guinea pigs which had received premedication with reserpine, was about the same as that of the racemate; whereas the negatively chronotropic action on the isolated, spontaneously beating right atrium was distinctly weaker than that of the racemate, and the comparison of the action of 1 mg/ml on the isolated atria of guinea pigs which had not received premedication with reserpine and of those which had, shows that, in contrast to the racemate, the compound of the formula I in this concentration does not have a cardiostimulating action.

On intravenous administration, the acute toxicity of the hydrochloride of the compound of the formula I in mice and rats is of about the same degree as that of the hydrochloride of the racemate, and, on oral administration, is somewhat lower. R-(−)-α-[methylamino)methyl]-9,10-ethanoanthracene-9(10)-ethanol and its pharmaceutically acceptable acid addition salts can be used as active ingredients for medicaments having sedative, antiaggressive, tranquillizing, antihistaminic and antidepressive action, especially for treating dysphoric conditions characterised by anxiety, depression or excitability, and psychovegetative or psychosomatic disorders stemming from depression and/or anxiety taking the form of a masked depression.

R-(−)-α-[(Methylamino)methyl]-9,10-ethanoanthracene-9(10H)-ethanol of the formula I and its acid addition salts are obtained according to the invention by (a) resolving the racemic α-[methylamino)methyl]-9,10-ethanoanthracene-9(10H)-ethanol and isolating R-(−)-α-[methylamino)methyl]-9,10-ethanoanthracene-9(10H)-ethanol, if desired in the form of an acid addition salt, or (b) reacting a compound of the formula II

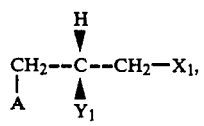

with a compound of the formula III $$X_2-CH_3 \qquad (III)$$

wherein one of $X_1$ and $X_2$ is the amino group and the other is a reactive esterified hydroxyl group, and $Y_1$ is a free hydroxyl group, and $X_1$ together with $Y_1$ can also be an epoxy group, and A is the 9,10-ethanoanthracen-9(10H)-yl radical, or (c) in a compound of the formula

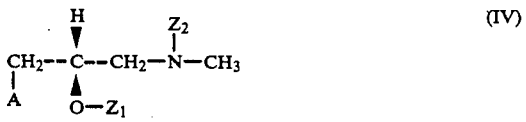

(IV)

in which at least one of $Z_1$ and $Z_2$ is a removable radical and the other may be hydrogen, or $Z_1$ and $Z_2$ together are a divalent removable radical, and A is the 9,10-ethanoanthracen-9(10H)-yl radical, removing $Z_1$ and/or $Z_2$, or (d) reducing a compound which differs from the compound of the formula I only in that, in said compound, a carbon atom adjacent to the nitrogen atom is attached to this latter through a double bond or is substituted by a hydroxyl group or an oxo radical, optionally together with lower alkoxy, or (e) the addition of ethylene to R-α-[(methylamino)methyl]-9(10H)-anthracene, or (f) reacting a compound of the general formula V

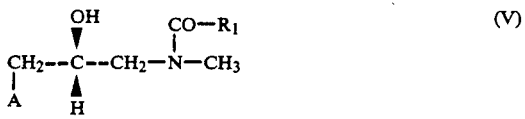

(V)

in which $R_1$ is an unsubstituted or substituted hydrocarbon radical or an unsubstituted or substituted heterocyclic radical, and A is the 9,10-ethanoanthracen-9(10H)-yl radical, with a strong oxygen-containing inorganic or organic acid or with a halide thereof, and hydrolysing the intermediate obtained, and, if desired, converting the resultant R-(−)-α-[(methylamino)methyl]-9,10-ethanoanthracene-9(10H)-ethanol into an acid addition salt and/or liberating the base from a resultant acid addition salt.

The resolution and isolation in accordance with process (a) is accomplished in a manner known per se. For example, it is possible to convert the racemate with salt-forming optically active acids, such as organic carboxylic or sulfonic acids, e.g. the (D)- and (L)-forms of tartaric acid, bis-0,0=-(p-toluoyl)-tartaric acid, malic acid, mandelic acid, camphorsulfonic acid, quinic acid, lactic acid, glutamic acid or asparaginic acid, into acid addition salts. The mixtures obtained of the corresponding salts can be resolved into the diastereoisomeric salts on the basis of physicochemical differences, e.g. the solubility or crystallisability, and, if desired, the optically active (−)-base liberated from the salt.

The (−)-base can also be separated from the racemate by fractional crystallisation from a suitable solvent, if appropriate also from an optically active solvent, or by chromatography, especially thin-layer chromatography, on an optically active carrier.

A reactive esterified hydroxyl group in a compound of the formula II or III is especially a hydroxyl group which is esterified with a strong organic or inorganic acid, in particular with a hydrohalic acid, such as hydrochloric, hydrobromic or hydriodic acid, or with an arylsulfonic acid, such as a benzenesulfonic acid which is mono-, di- or polysubstituted by lower alkyl or alkoxy radicals, e.g. those mentioned above, or by halogen atoms, such as chlorine or bromine atoms, e.g. p-toluenesulfonic acid or p-bromobenzenesulfonic acid, or with a lower alkanesulfonic acid, e.g. methanesulfonic acid, or, especially as $X_2$, also a hydroxyl group esterified by sulfuric or methylsulfuric acid. $X_1$ together with $Y_1$ can also form an epoxy bridge.

The reaction according to process (b) is carried out in conventional manner, preferably in the presence of a solvent and, if desired, in the presence of a condensation agent, e.g. a basic condensation agent, preferably at elevated temperature and optionally in a closed vessel under pressure. A basic condensation agent is e.g. an alkali hydroxide or carbonate, e.g. sodium hydroxide or potassium carbonate, or a tertiary amine, e.g. triethylamine or pyridine.

In the starting materials of the general formula IV for process (c), removable radicals $Z_1$ and $Z_2$, as also divalent removable radicals formed by $Z_1$ and $Z_2$ together, are radicals which can be removed e.g. by solvolysis, especially hydrolysis, or by reduction, e.g. hydrogenolysis.

Suitable radicals $Z_1$ and $Z_2$ which are removable by solvolysis, especially hydrolysis, are e.g. acyl radicals, such as alkanoyl radicals, especially unsubstituted or halogenated, e.g. fluorinated, lower alkanoyl radicals, such as the acetyl radical or the trifluoroacetyl radical, and also e.g. aroyl and aryl-lower alkanoyl radicals, such as the benzoyl or phenylacetyl radical, or acyl radicals of carbonic acid hemiesters, e.g. lower alkoxycarbonyl radicals, such as the methoxycarbonyl, ethoxycarbonyl or tert-butoxycarbonyl radical, or aralkoxycarbonyl radicals, such as the benzyloxycarbonyl radical, as well as e.g. silyl radicals, such as the trimethylsilyl radical.

A divalent radical formed by $Z_1$ and $Z_2$ is e.g. a geminal divalent hydrocarbon radical, especially a lower alkylidene radical, such as the methylene, ethylidene or 1-methylethylidene radical (isopropylidene radical), or an aralkylidene radical, such as the benzylidene radical, and e.g. a phosphorylidene group, especially a lower alkoxyphosphorylidene group, such as the methoxy- or ethoxyphosphorylidene group.

The removal of $Z_1$ and/or $Z_2$ by hydrolysis is carried out with hydrolysing agents, e.g. in the present of acids, e.g. dilute mineral acids, such as sulfuric acid or hydrohalic acids, especially hydrochloric acid, or if $Z_1$ and $Z_2$ are acyl radicals, preferably in the presence of bases, e.g. alkali metal hydroxides, such as sodium hydroxide, in suitable organic or organic-aqueous solvents, at low temperature, e.g. at room tmeperature, or preferably with heating. The removal of a divalent radical formed by $Z_1$ and $Z_2$ by hydrolysis can effected in analogous manner.

Radicals $Z_1$ and $Z_2$ which are removable by reduction are e.g. 1-aryl-lower alkyl radicals, such as the benzyl radical, or 1-aryl-lower alkoxycarbonyl radical, such as the benzoyloxycarbonyl radical, which can be removed e.g. by hydrogenolysis, for example by reduction with catalytically activated hydrogen, such as hydrogen in the presence of a hydrogenation catalyst, e.g. a palladium or platinum catalyst. Aralkylidene radicals, such as the benzylidene radical, formed by $Z_1$ and $Z_2$ together can likewise be removed by hydrogenolysis. However, $Z_1$ or $Z_2$ can also be a 2-haloalkoxycarbonyl radical, e.g. the 2,2,2-trichloroethoxycarbonyl radical or the 2-iodoethoxycarbonyl radical, which can be removed by reduction. A suitable method of reduction is metallic reduction (nascent hydrogen), e.g. the action of metal or metal alloys and also amalgams, preferably in the presence of hydrogen donors, such as carboxylic acids, alcohols or water. In particular, zinc or zinc alloys in acetic acid are used. Further suitable reducing agents are chromium(II) compounds, such as chromium(II) chloride or chromium(II) acetate. $Z_2$ can also be an arylsulfonyl group, such as the toluenesulfonyl group, which can be removed in conventional manner by reduction with nascent hydrogen, e.g. by an alkali metal, such as lithium or sodium, in liquid ammonia. The removal of an arylsulfonyl group can also be accomplished with a hydride, e.g. one of the simple or complex hydrides mentioned above in connection with process (c), preferably lithium aluminium hydride, advantageously in the presence of an inert solvent, such as an ethereal organic solvent, e.g. tetrahydrofurane.

Starting materials for process (d) containing a double bond between the nitrogen atom and an adjacent carbon atom are R-α-[(methyleneamino)-methyl]-9,10-ethanoanthracene-9(10H)-ethanol and R-α-[(methylimino)-methyl]-9,10-ethanoanthracene-9(10H)-ethanol. The compounds which are substituted in the adjacent position to the nitrogen atom by hydroxyl are R-α-[(hydroxymethylamino)methyl-9,10-ethanoanthracene-9(10H)-ethanol and R-1-(methylamino)-9,10-ethanoanthracene-9(10H)-propane-1,2-diol. The reduction of the above mentioned four compounds can be carried out in conventional manner, preferably with a simple or complex hydride, e.g. a borane, or with a di-light metal hydride, e.g. an alkaline earth metal hydride, such as sodium borohydride or lithium aluminium hydride, or with an alkoxyaluminium hydride or alkoxyborohydride, e.g. one of those referred to hereinafter.

It is also possible, however, to perform the reduction as a hydrogenation with hydrogen in the presence of a catalyst, such as a platinum, palladium or nickel catalyst, or of a homogeneous catalyst, e.g. a complex rhodium compound, such as a rhodium chlorotriphenylphosphine complex.

If a carbon atom adjacent to the nitrogen atom is substituted by an oxo radical, the corresponding starting compounds are, on the one hand, R-N-methyl-9,10-ethanoanthracene-9(10H)-lactamide and, on the other, N-[3-(9,10-ethanoanthracen-9(10H)-yl)-2(R)-hydroxypropyl]-formamide, as well as lower alkyl esters of carbamic acid which are substituted at the nitrogen atom by the same radical, such as the methyl and ethyl ester. Their reduction can be carried out by the conventional methods of amide reduction, for example with a simple or complex hydride, such as a borane, e.g. diborane, or with a complex di-light metal hydride, especially an alkali metal aluminium hydride, such as lithium or sodium aluminium hydride, in an ethereal solvent, such as diethyl ether or tetrahydrofurane, or with an alkali metal alkoxyaluminium hydride or alkali metal alkoxyborohydride, e.g. sodium dibutoxy aluminium hydride or sodium trimethoxy borohydride, or with an alkaline earth metal aluminium hydride, such as magnesium aluminium hydride, or with sodium borohydride in a tertiary amine, such as pyridine or triethylamine, or with aluminium hydride-aluminium chloride.

The introduction of the 9,10-ethano radical in accordance with process (e) can be effected in conventional manner, e.g. by reaction of the anthracene derivative with ethylene by the Diels-Alder method, advantageously in a suitable solvent, such as an aromatic hydrocarbon, e.g. benzene or toluene, and at elevated temperature, e.g. in the range from 50° to 250° C., and/or under pressure, e.g. at 2 to 150 atoms.

In the starting materials of the general formula V for process (f), an unsubstituted or substituted hydrocarbon radical $R_1$ is e.g. lower alkyl, such as ethyl, propyl, isopropyl, butyl or tertbutyl, and especially methyl, as well as e.g. phenyl-lower alkyl, such as benzyl or 2-phenylethyl, or phenyl, whilst in these or other radicals $R_1$ substituents can be e.g. halogen up to atomic number 35, lower alkyl, e.g. methyl, lower alkoxy, e.g. methoxy, or aryloxy, e.g. phenoxy. As a heterocyclic radical, $R_1$ is e.g. furyl, such as 2-furyl, thienyl, such as 2-thienyl, or pyridinyl, such as 3- or 4-pyridinyl.

The corresponding starting materials of the formula V can be obtained by conventional acylation methods from the free S-(+)-α-[(methylamino)methyl]-9,10-ethanoanthracene-9(10H)-ethanol obtained as by-product in the separation of racemic α-[methylamino)methyl]-9,10-ethanoanthracene-9(10H)-ethanol, in particular using carboxylic acid halides or lower alkyl esters, or, especially for obtaining the compound in which $R_1$ is methyl and which is a particularly suitable starting material, using anhydrides, such as acetic anhydride.

Suitable oxygen-containing inorganic or organic acids in process (f) are in particular concentrated sulfuric acid or phosphoric acid and also strong organic sulfonic acids such as aliphatic sulfonic acids, e.g. methanesulfonic acid, or aromatic sulfonic acids, such as an unsubstituted or substituted phenylsulfonic acid, e.g. 4-methyl-, 4-bromo-, 4-nitro- or 2,4-dinitrophenylsulfonic acid, or naphthalenesulfonic acids, e.g. 1-naphthalenesulfonic acid. Suitable halides of these acids are especially the chlorides or bromides, in particular thionyl chloride, and also e.g. thionyl bromide, sulfuryl chloride, chlorosulfonic acid, phosphorus trichloride, phosphorus pentachloride, phosphoroxy chloride or methanesulfonyl chloride. It is also possible to employ mixed ester halides corresponding to the above halides of polyvalent acids, such as a lower alkoxysulfonyl halide, e.g. methoxy- or ethoxysulfonyl chloride, or lower alkyl ester halides of phosphoric acid, e.g. dimethylphosphoryl chloride.

The reactions with strong acids, especially concentrated sulfuric acid or phosphoric acid, are carried out in the presence or absence of solvents or diluents, e.g. acetic anhydride, in the temperature range from about −50° to +200° C., and the reactions with acid halides, e.g. thionyl chloride, are carried out also in the presence or absence of solvents° or diluents, e.g. hydrocarbons or especially chlorinated hydrocarbons, such as methylene chloride, in the temperature range from about 31 10° to +70° C., preferably from about +10° to +50° C. It may be assumed that the reaction products of these reactions are 2-$R_1$-5-(9,10-ethanoanthracen-9(10H)-yl)-4,5-dihydro-3-methyl-oxazolium salts, the anion of which corresponds to the acid employed in the reaction or, if the reactions are carried out with acid halides, is the corresponding halogen ion.

The hydrolysis of the intermediates is carried out in acid or basic medium. Suitable acids are e.g. aqueous acids, such as aqueous mineral acids, e.g. aqueous hydrochloric acid, sulfuric acid or phosphoric acid. The acid hydrolysis is carried out in a temperature range from 0° to 120° C., advantageously from 10° to 50° C. Examples of suitable bases are aqueous lyes, such as those of alkali metals or alkaline earth metals, such as sodium hydroxide or potassium hydroxide, or the hydroxides of calcium or magnesium, and the cited reagents are advantageously employed at elevated temperature, e.g. in the range from 50° to 150° C.

The hydrolysis can be carried out stepwise by hydrolysing an intermediate, optionally via the corresponding free base as intermediate stage, in aqueous medium, to produce the corresponding N-acyl compound of the general formula V having inverse steric configuration to that of the respective starting material of the formula V, and subsequently hydrolysing this compound to a compound of the formula I.

The process according to (f) can also advantageously be carried out by reacting a starting material of the general formula V obtained directly beforehand without isolating it in the pure form, in the same batch with a suitable acid or halide thereof, and hydrolysing the intermediate thereby obtained, likewise without further purification.

The optically active starting materials required for processes (b) to (e) can be obtained either by resolution of known racemic, especially basic, starting materials in a manner known per se, or in a manner analogous to that employed for obtaining the racemic starting materials required for the preparation of the known racemate using optically active instead of racemic precursors.

Acid addition salts, especially pharmaceutically acceptable acid addition salts, of the compound of the formula I, e.g. those referred to above, can be obtained in conventional manner. For example, a solution of the base in an organic solvent, e.g. methylene chloride, ethyl acetate, ethanol or isopropanol, is reacted with the acid desired as salt component, or with a solution thereof in the same or another organic solvent, such as ethyl acetate or diethyl ether, and, if desired after cooling or concentrating or after addition of a solvent having poorer solubility for salts, e.g. diethyl ether, collecting the precipitated salt by filtration.

The present invention also relates to the compound of the formula I and the pharmaceutically acceptable acid addition salts thereof for use as medicaments, especially as antidepressants, sedatives or antihistamines, e.g. for treating the disorders mentioned above, and also to their use for the production of corresponding pharmaceutical compositions.

The dosage of the compound of the formula I and its pharmaceutically acceptable acid addition salts for warm-blooded animals depends on the species, body weight and age, and on the individual condition and the mode of application. The daily doses are between about 0.05 and 3.0 gm/kg, preferably between about 0.08 and 1.5 mg/kg of body weight. On average, a daily dose of about 10 to about 150 mg, preferably about 30 to about 75 mg, will be administered to a warmblooded animal having a body weight of about 70 kg.

The present invention also relates to pharmaceutical compositions which contain the compound of the formula I or pharmaceutically acceptable acid addition salts thereof. The pharmaceutical compositions of the invention are in particular those for enteral, such as oral or rectal as well as parenteral, administration, which contain the pharmacologically active ingredient alone or preferably together with at least one pharmaceutically acceptable carrier. Such compositions contain the active ingredient, i.e. the compound of the formula I or a pharmaceutically acceptable acid addition salt thereof, in an amount and concentration suitable for the administration of the above daily doses in one or more, preferably three, single doses.

Pharmaceutical compositions of the invention in dosage unit formulations, such as sugar-coated tablets, tablets, capsules, suppositories or ampoules, contain, as active ingredient in each dosage unit, preferably 2.5 to 50 mg, especially 5 to 25 mg, of the compound of the formula I or preferably of a pharmaceutically acceptable acid addition salt of this base, together with at least one pharmaceutical carrier.

Dosage unit formulations for peroral administration contain, as active ingredient, preferably between 1% and 50% of the compound of the formula I or of a pharmaceutically acceptable acid addition salt thereof. They are prepared by combining the active ingredient e.g. with solid pulverulent carriers, such as lactose, saccharose, sorbitol, mannitol; starches, such as potato starch, maize starch or amylopectin, and also laminaria or powdered citrus pulp; cellulose derivatives or gelatin, optionally with the addition of glidants, such as magnesium or calcium stearate or polyethylene glycols, to produce tablets or cores for sugar-coated tablets. The tablet cores are coated e.g. with concentrated sugar solutions which additionally contain e.g gum arabic, talc and/or titaniumdioxide or with a lacquer which is dissolved in mobile organic solvents or solvent mixtures. Colourants can be added to these coatings, e.g. to identify different doses of active ingredient.

Further suitable dosage unit formulations for oral administration are dry-filled capsules made of gelatin and also soft sealed capsules made from gelatin and a plasticiser, such as glycerol. The dry-filled capsules can contain the active ingredient in the form of granules, for example in admixture with fillers such as maize starch, binders and/or lubricants, such as talc or magnesium stearate, and optionally stabilisers, such as sodium metabisulfite ($Na_2S_2O_5$) or ascorbic acid. In soft capsules, the active ingredients are preferably dissolved or suspended in suitable liquids, for example in liquid polyethylene glycols, to which stabilisers can also be added.

Suitable dosage formulations for rectal administration are e.g. suppositories, which consist of a combination of an active ingredient with a suppository base. Examples of suitable suppository bases are natural or synthetic triglycerides, paraffin hydrocarbons, polyethylene glycols or higher alcohols. Gelatin rectal capsules, which consist of a combination of the active ingredient with a base material, can also be employed. Suitable base materials are e.g. liquid triglycerides, polyethylene glycols or paraffin hydrocarbons.

Ampoules for parenteral, especially intramuscular, administration preferably contain a water-soluble pharmaceutically acceptable salt of the compound of the formula I in a preferred concentration of 0.5 to 5%, optionally together with suitable stabilisers and buffer substances, in aqueous solution.

The following Examples illustrate the production of the compound of the formula I and also of a number of typical dosage unit formulations, but are not to be construed as implying any restriction of the scope of the invention.

EXAMPLE 1

184.8 g (0.63 mole) of racemic α-[(methylamino)methyl]9,10-ethanoanthracene-9(10H)-ethanol and 127.5 g (0.315 mole) of (−)-bis-0,0′-(p-toluoyl)-L-tartaric acid are dissolved in 2500 ml of methanol at a temperature up to 40° C. and the solution is then allowed to stand at room temperature for 24 hours. The precipitated crystals are filtered with suction and washed with two 50 ml portions of ice-cold methanol. If desired, the filtrate can be used for obtaining the other antipode. The filter cake is dissolved in 2500 ml of hot methanol and the solution is concentrated to a volume of 80 ml by distilling off methanol. This solution is allowed to stand for 24 hours at room temperature, whereupon R-(−)-α-[(methylamino) methyl]-9,10-ethanoanthracene-9(10H)-ethanol (−)-bis-0,0'-(p-toluoyl)-L-tartrate-(1:1) crystallises out. The crystalline precipitate is filtered with suction, washed with two 40 ml portions of ice-cold methanol and dried in a water jet vacuum at 50° C.

Melting point: 180° C. (with decomposition). $[α]_D^{20} = -64°$ (c=1.135 in methanol).

The free base is obtained by dissolving 4.9 g (0.01 mole) of the above salt in 50 ml of methylene chloride, extracting the solution with two 15 ml portions of 1N sodium hydroxide, then washing the extracts with two 15 ml portions of water and concentrating them at about 14 mbar. The residual crystallised R-(−)-α-[(methylamino)methyl]-9,10-ethanoanthracene-9(10H)-ethanol melts at 107°-108° C.; $[α]_D^{20} = -9.1$ (c=1.01 in methanol).

If desired, the base can additionally be recrystallised from ether. The hydrochloride is obtained by dissolving 56.9 g of R-(−)-α-[(methylamino)methyl]-9,10-ethanoanthracene-9(10H)-ethanol (−)-bis-0,0'-(p-toluoyl)-L-tartrate-(1:1) in 200 ml of methylene chloride and, with stirring, adding at room temperature an ethereal solution of hydrogen chloride until the supernatant vapours permanently colour Congo paper blue. The hydrochloride of R-(−)-α-[(methylamino)methyl]-9,10-ethanoanthracene-9(10H)-ethanol crystallises out in the process. After addition of 300 ml of ether, the crystals are filtered with suction and then recrystallised once from ethanol/methanol.

The purified hydrochloride melts at 231° to 232° C.; $[α]_D^{20} = -9°$ (C=1.37 in methanol).

EXAMPLE 2

(a) 1.9 ml of acetic anhydride are added dropwise at 5°-10° C. to a solution of 2.93 g (0.010 mole) of S-(+)-α-[(methylamino)methyl]-9,10-ethanoanthracene-9(10H)-ethanol in 8 ml of dimethyl formamide. The solution is stirred for 4 hours at room temperature, then poured into 60 ml of water and extracted with 100 ml of ethyl acetate. The ethyl acetate solution is washed with saturated sodium bicarbonate solution, dried over sodium sulfate and concentrated in vacuo. The residual crude S-(+)-α-[(N-methylacetamido) methyl]-9,10-ethanoanthracene-9(10H)-ethanol can be further processed direct.

(b) The crude product of (a) (2.5 g) is dissolved in 6 ml of methylene chloride. With stirring, a solution of 0.77 ml of thionyl chloride in 4 ml of methylene chloride is added at 5°-10° C. in the course of 15 minutes. The reaction solution is stirred for 2 hours at 20° C. and then for 1 hour at 35° C., and subsequently evaporated to dryness at about 14 mbar (water jet vacuum).

(c) The residue of (b) is dissolved in 10 ml of ethanol, then 2.5 ml of water and 1.6 g of sodium hydroxide are added and the mixture is refluxed for 3 hours. The reaction mixture is then concentrated at about 14 mbar and, after addition of 50 ml of ice-water, extracted with 100 ml of ethyl acetate. The ethyl acetate solution is washed neutral with water, dried over sodium sulfate, and concentrated at about 14 mbar, affording as residue the crude base with inverted configuration. The residue is dissolved in 10 ml of methylene chloride and the hydrochloride of R-(−)-α-[(methylamino)methyl]-9,10-ethanoanthracene-9(10H)-ethanol is precipitated by addition of ethereal hydrogen chloride solution. The crystals are filtered with suction and recrystallised from isopropanol Melting point 229°-231° C.; $[α]_D^{20} = -9 \pm 1°$ (c=1.6 in methanol).

The starting material for (a) is obtained as follows:

The filtrate mentioned in Example 1 which contains the antipode is concentrated at about 14 mbar. The residue is dissolved in 500 ml of methylene chloride and this solution is extracted with three 100 ml portions of 2N sodium hydroxide solution and then with two 100 ml portions of water. The methylene chloride is evaporated off, affording 132.5 g of base which is partially enriched with S-(+)-α-[methylamino)methyl]-9,10-ethanoanthracene-9(10H)-ethanol. This base (0.452 mole) and 91.4 g (0.226 mole) of (+)-bis-0,0'-(p-toluoyl)-D-tartaric acid are dissolved in 1800 ml of methanol at 40° C. and the solution is allowed to stand for 24 hours at room temperature. The precipitated crystals are filtered with suction and dissolved in methanol. This solution is concentrated to about a third of its volume and allowed to stand for 24 hours at room temperature. The precipitated crystals are filtered with suction and washed with a small amount of methanol, affording S-(+)-α-[(methylarsino)methyl]-9,10-ethanoanthracene-9(10H)-ethanol (+)-bis-0,0'-(p-toluoyl)-D-tartrate (1:1), which melts at 178° C. with decomposition; $[α]_D^{20} = +63°$ (c=0.774 in methanol). The base is decomposition; $= +63°$ liberated by dissolving 88.4 g (0.18 mole) of the above salt in 500 ml of methylene chloride and extracting this solution with three 100 ml portions of 2N sodium hydroxide solution and then with two 100 ml portions of water. The methylene chloride is evaporated off and the residual S-(+)-α-[methylamino)methyl]-9,10-ethanoanthracene-9(10H)-ethanol (m.p. 106°-107° C.) can be used direct for the acetylation according to (a).

EXAMPLE 3

2.93 g (0.010 mole) of S-(+)-α-[methylamino)methyl]-9,10-ethanoanthracene-9(10H)-ethanol are dissolved in portions in 14 ml of acetic anhydride. To this solution is added, with stirring, a solution of 1.75 g of 96% sulfuric acid in 6 ml of acetic anhydride and the mixture is then refluxed for 3 hours. The resultant solution is concentrated at about 14 mbar and the reaction product resulting from N-acetylation and cyclisation is taken up in 30 ml of 1N sulfuric acid and the solution is refluxed for 2 hours. After addition of 50 g of ice the mixture is adjusted with aqueous ammonia solution to pH 9 and extracted with two 50 ml portions of ethyl acetate. The combined organic phases are dried over sodium sulfate and evaporated to dryness. The residual crude base is dissolved in 10 ml of methylene chloride and the hydrochloride of R-(−)-α-[(methylamino)methyl]-9,10-ethanoanthracene-9(10H)-ethanol is precipitated by addition of ethereal hydrogen chloride solution. The precipitated crystals are filtered with suction and recrystallised from isopropanol. Melting point: 228°-230° C.

EXAMPLE 4

3.9 g of the crude 5-(R)-[(9,10-ethanoanthracen-9(10H)-yl)methyl]-3-methyl-oxazolidine and 60 ml of 2N hydrochloric acid are heated for 3 hours to 90° C. Then 5N sodium hydroxide is added until the reaction is alkaline. The reaction mixture is extracted with methylene chloride and the organic phase is concentrated. The residual crude R-α-(−)-[methylamino)methyl]-9,10-ethanoanthracene-9(10H)-ethanol is dissolved in 10 ml of ethanol and 1 ml of a 10% ethanolic hydrogen chloride solution is added. The hydrochloride of the above base is crystallised by addition of ether. The crystallised hydrochloride is filtered with suction and, if desired, further Purified as in Example 1 or 2.

The starting material can be obtained as follows:

(a) 20.0 g of R-α-(aminomethyl)-9,10-ethanoanthracene-9(10H)-ethanol (obtainable e.g. in analogy to Example 1 above from the corresponding racemic compound with a melting point of 176°-177° C. described in U.S. Pat. No. 4,017,542, Example 1) are heated in a mixture of 10 ml of 35% aqueous formaldehyde solution and 150 ml of formic acid for 1 hour to 95° C. The reaction mixture is concentrated in vacuo and the residue is made alkaline by addition of 2N sodium hydroxide and extracted with methylene chloride. The organic phase is concentrated, affording as residue 5(R)-[(9,10-ethanoanthracen-9-(10H)-yl)methyl]-3-methyl-oxazolidine.

EXAMPLE 5

To a suspension of 0.7 g of lithium aluminium hydride in 20 ml of tetrahydrofurane is added a solution of 1.5 g of N-[3-(9,10-ethanoanthracen-9(10H)-yl)-2(R)-hydroxypropyl]-formamide in 20 ml of tetrahydrofurane, and the mixture is refluxed for 4 hours. The reaction mixture is cooled, then 1.4 ml of water are added, followed by the subsequent addition of 1.4 ml of 15% sodium hydroxide and a further 5 ml of water. The precipitate is collected by filtration and the filtrate is concentrated and the residue dissolved in 2N acetic acid. The acid solution is washed with ether and then 10% sodium hydroxide is added until the reaction is alkaline. The solution is extracted with methylene chloride, then the solvent is evaporated off and the residual crude R-(−)-α-(methylamino)methyl]-9,10-ethanoanthracene-9(10H)-ethanol is converted into the hydrochloride with a melting point of 231° -232° C. as described in Example 1 or 2.

The substituted formamide employed as starting material can be obtained as follows:

(a) (R)-α-(Aminomethyl)-9,10-ethanoanthracene-9(10H)-ethanol (cf. Example 4a) are refluxed for 2 hours in 75 ml of ethyl formate. The cooled solution is evaporated to dryness at about 14 mbar. The residue is dissolved in 75 ml of methylene chloride and this solution is washed with 40 ml of 1N hydrochloric acid, dried over sodium sulfate, and again evaporated to dryness at about 14 mbar. The residual N-[3-(9,10-ethanoanthracen-9(10H)-yl)-2(R)-hydroxypropyl]-formamide can be used direct for the reduction.

EXAMPLE 6

In an autoclave, a soltuion of 1- g of R-α-[(methylamino) methyl]-anthracene-9(10H)-ethanol in 200 ml of benzene is heated under a pressure of 70 atmos. for 6 hours to 70° C. The solution is then extracted with 200 ml of 2N hydrochloric acid. The acid extract is made alkaline and extracted with methylene chloride. The organic phase is concentrated and the residual crude R-α-(−)-[methylamino) methyl]-9,10-ethanoanthracene-9(10H)-ethanol is converted into its hydrochloride as described in Example 1.

EXAMPLE 7

(a) 100 g of the hydrochloride of R-(−)-α-[(methylamino) methyl]-9,10-ethanoanthracene-9-(10H)-ethanol are mixed with 202 g of lactose and 195 g of potato starch. The mixture is moistened with an alcoholic solution of 10 g of stearic acid and granulated through a sieve. After it has been dried, the granulate is mixed with 200 g of potato starch, 250 g of talc, 3.0 g of magnesium stearate and 40 g of colloidal silica, and the mixture is compressed to 10,000 tablets each weighing 100 mg and containing 10 mg of active ingredient. The tablets can be provided with a breaking notch for a finer adjustment of the dose.

(b) A granulate is prepared from 50 g of the hydrochloride of R-(−)-α-[(methylamino)methyl]-9,10-ethanoanthracene-9-(10H)-ethanol, 228.40 g of lactose and an alcoholic solution of 7.5 g of stearic acid. After it has been dried, this granulate is mixed with 56.60 g of colloidal silica, 200 g of talc, 20 g of potato starch and 2.50 g of magnesium stearate, and the mixture is compressed to 10,000 sugar-coated tablet cores. These cores are then coated with a concentrated syrup consisting of 417.3 g of crystalline saccharose, 6 g of shellac, 10 g of gum arabic, 0.2 g of colourant and 1.5 g of titanium dioxide, and dried. Each coated tablet weighs 120 mg and contains 5 mg of active ingredient.

(c) 1000 capsules each containing 10 mg of active ingredient are prepared as follows: 10 g of hylrochloride of R-(−)-α-[methylamino) methyl]-9,10-ethanoanthracene-9-(10H)-ethanol are mixed with 263 g of lactose and the mixture is moistened uniformly with an aqueous solution of 2 g of gelatin and granulated through a suitable sieve (e.g. sieve III in Ph. Helv. V). The resultant granulate is mixed with 10 g of dried maize starch and 15 g of talc, and the mixture is packed uniformly into 1000 size 1 hard gelatin capsules.

(d) 100 suppositories each containing 20 mg of active ingredient are prepared from a suppository base material consisting of 20 g of hydrochloride of R-(−)-α-[methylamino)methyl]-9,10-ethanoanthracene-9-(10H)-ethanol and 168.0 g of adeps solidus.

(e) 1000 ampoules are filled with a solution of the hydrochloride of R-(−)-α-[(methylamino)methyl]-9,10-ethanoanthracene-9-(10H)-ethanol in 1 litre of water and sterilised. One ampoule contains a 2.5% solution of 25 mg of active ingredient.

What is claimed is:

1. A method of treating a dysphoric condition characterized by anxiety, depression or excitability in a warm-blooded animal in need of such treatment comprising administering, enterally or parenterally, to said animal a therapeutically effective amount for said condition of a compound of the formula

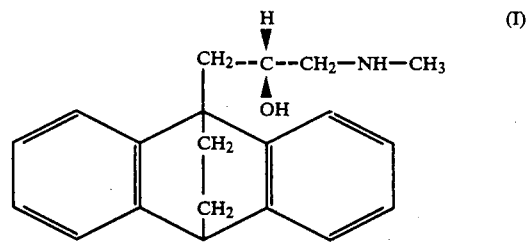

which is R-(−)-alpha-[(methylamino)methyl]-9,10-ethanoanthracene-9(10H)-ethanol, substantially free of the S-(+) antipode thereof, or a pharmaceutically acceptable salt thereof.

2. A method of treating a psychovegetative disorder stemming from depression or anxiety in a warm blooded animal in need of such treatment comprising administering, enterally or parenterally, to said animal a therapeutically effective amount for said condition of a compound of the formula

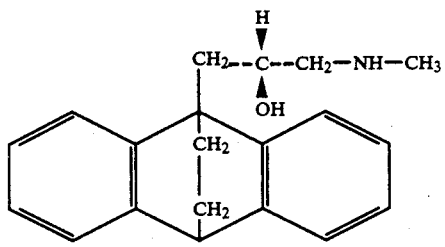

which is R-(−)-alpha-[(methylamino)methyl]-9,10-ethanoanthracene-9(10H)-ethanol, substantially free of the S-(+) antipode thereof, or a pharmaceutically acceptable salt thereof.

3. A method of treating a psychosomatic disorder stemming from depression or anxiety in a warm-blooded animal in need of such treatment comprising administering, enterally or parenterally, to said animal a therapeutically effective amount for said condition of a compound of the formula

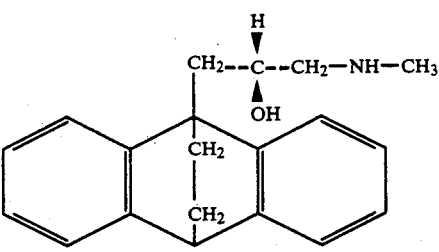

which is R-(−)-alpha-[(methylamino)methyl]-9,10-ethanoanthracene-9(10H)-ethanol, substantially free of the S-(−) antipode thereof, or a pharmaceutically acceptable salt thereof.

4. The method of claim 1 wherein said compound or pharmaceutically acceptable salt thereof is administered in an amount of from 0.05 and 3.0 mg/kg/day.

5. The method of claim 2 wherein said compound or pharmaceutically acceptable salt thereof is administered in an amount of from 0.05 and 3.0 mg/kg/day.

6. The method of claim 3 wherein said compound or pharmaceutically acceptable salt thereof is administered in an amount of from 0.05 and 3.0 mg/kg/day.

7. The method of claim 1 wherein said compound or pharmaceutically acceptable salt thereof is administered in an amount of from 10 and 150 mg/day.

8. The method of claim 2 wherein said compound or pharmaceutically acceptable salt thereof is administered in an amount of from 10 and 150 mg/day.

9. The method of claim 3 wherein said compound or pharmaceutically acceptable salt thereof is administered in an amount of from 10 and 150 mg/day.

* * * * *